US011359218B2

(12) United States Patent
Bootsma

(10) Patent No.: US 11,359,218 B2
(45) Date of Patent: *Jun. 14, 2022

(54) OIL COMPOSITION AND METHOD OF RECOVERING SAME

(71) Applicant: Poet Research, Inc., Sioux Falls, SD (US)

(72) Inventor: Jason Bootsma, Sioux Falls, SD (US)

(73) Assignee: Poet Research, Inc., Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/674,622

(22) Filed: Nov. 5, 2019

(65) Prior Publication Data

US 2020/0063168 A1 Feb. 27, 2020

Related U.S. Application Data

(60) Continuation of application No. 15/631,420, filed on Jun. 23, 2017, now Pat. No. 10,526,623, which is a
(Continued)

(51) Int. Cl.
*C12P 7/64* (2022.01)
*C10L 1/02* (2006.01)
(Continued)

(52) U.S. Cl.
CPC .............. *C12P 7/64* (2013.01); *C10L 1/026* (2013.01); *C11C 1/005* (2013.01); *C11C 1/045* (2013.01); *C11C 1/08* (2013.01); *C12P 7/6409* (2013.01); *C10L 2200/0476* (2013.01); *C10L 2290/26* (2013.01); *Y02E 50/10* (2013.01)

(58) Field of Classification Search
CPC ............ C10L 1/026; C10L 2200/0476; C10L 2290/26; C11C 1/005; C11C 1/045; C11C 1/08; C12P 7/64; C12P 7/6409; Y02E 50/10; Y02E 50/13; Y02E 50/0476
See application file for complete search history.

(56) References Cited

U.S. PATENT DOCUMENTS

| 2,310,184 A | | 2/1943 | Schopmeyer | |
| 3,629,307 A | * | 12/1971 | Marino et al. | ............ C11B 3/06 554/203 |

(Continued)

FOREIGN PATENT DOCUMENTS

| CA | 1230546 | 12/1987 |
| EP | 0 825 81 | 6/1983 |

(Continued)

OTHER PUBLICATIONS

U.S. Appl. No. 14/139,671, filed Dec. 23, 2013, Bootsma, Jason.
(Continued)

*Primary Examiner* — Latosha Hines
(74) *Attorney, Agent, or Firm* — Honigman LLP

(57) ABSTRACT

The present invention generally relates to oil compositions and methods of producing such oil compositions. More particularly, the present invention relates to an oil composition recovered from a fermentation product as well as methods of recovering such oil compositions for use in various processes such as bio-diesel production as well as in various edible applications.

23 Claims, 1 Drawing Sheet

Related U.S. Application Data continuation of application No. 14/139,671, filed on Dec. 23, 2013, now Pat. No. 9,695,449, which is a division of application No. 12/208,127, filed on Sep. 10, 2008, now Pat. No. 8,702,819.

(51) Int. Cl.
*C11C 1/00* (2006.01)
*C11C 1/04* (2006.01)
*C11C 1/08* (2006.01)
*C12P 7/6409* (2022.01)

(56) References Cited

U.S. PATENT DOCUMENTS

| | | | |
|---|---|---|---|
| 4,284,652 | A | 8/1981 | Christensen |
| 4,341,713 | A | 7/1982 | Stolp et al. |
| 4,466,889 | A | 8/1984 | Miller et al. |
| 4,721,706 | A | 1/1988 | Bessler et al. |
| 5,397,834 | A | 3/1995 | Jane et al. |
| 5,406,768 | A | 4/1995 | Giuseppe et al. |
| 5,441,801 | A | 8/1995 | Deaner et al. |
| 5,486,553 | A | 1/1996 | Deaner et al. |
| 5,497,594 | A | 3/1996 | Giuseppe et al. |
| 5,516,472 | A | 5/1996 | Laver |
| 5,518,677 | A | 5/1996 | Deaner et al. |
| 5,539,027 | A | 7/1996 | Deaner et al. |
| 5,578,090 | A | 11/1996 | Bradin |
| 5,596,080 | A | 1/1997 | Pelosi |
| 5,635,123 | A | 6/1997 | Riebel et al. |
| 5,725,939 | A | 3/1998 | Nishibori |
| 5,739,015 | A | 4/1998 | Srinivasan |
| 5,746,958 | A | 5/1998 | Gustafsson et al. |
| 5,851,469 | A | 12/1998 | Muller et al. |
| 5,914,367 | A | 6/1999 | Dordick et al. |
| 5,948,524 | A | 9/1999 | Seethamraju et al. |
| 6,054,207 | A | 4/2000 | Finley |
| 6,122,877 | A | 9/2000 | Hendrickson et al. |
| 6,313,105 | B1 | 11/2001 | Bengs et al. |
| 6,323,265 | B1 | 11/2001 | Bengs et al. |
| 6,527,532 | B1 | 3/2003 | Muller et al. |
| 6,593,625 | B2 | 7/2003 | Christiansen et al. |
| 6,648,930 | B2 | 11/2003 | Ulrich et al. |
| 6,703,227 | B2 | 3/2004 | Jakel et al. |
| 7,214,414 | B2 | 5/2007 | Khemani et al. |
| 7,601,858 | B2 | 10/2009 | Cantrell et al. |
| 7,638,644 | B2 | 12/2009 | Lee et al. |
| 9,394,505 | B2 | 7/2016 | Sticklen et al. |
| 2002/0151733 | A1 | 10/2002 | Ulrich et al. |
| 2003/0023109 | A1 | 1/2003 | Schlosberg et al. |
| 2003/0083512 | A1* | 5/2003 | Jakel ............... A23K 20/163 554/10 |
| 2003/0180415 | A1 | 9/2003 | Stiefel et al. |
| 2003/0180897 | A1 | 9/2003 | Ulrich et al. |
| 2003/0232109 | A1 | 12/2003 | Dawley et al. |
| 2004/0022881 | A1 | 2/2004 | Hauptmann et al. |
| 2004/0234649 | A1 | 11/2004 | Lewis et al. |
| 2004/0241254 | A1 | 12/2004 | Kopas et al. |
| 2005/0019545 | A1 | 1/2005 | Riebel |
| 2005/0101700 | A1 | 5/2005 | Riebel |
| 2006/0041152 | A1 | 2/2006 | Cantrell et al. |
| 2006/0041153 | A1* | 2/2006 | Cantrell ............... C11B 1/00 554/8 |
| 2006/0173169 | A1* | 8/2006 | Cheryan ............ A23K 20/147 530/373 |
| 2007/0238891 | A1* | 10/2007 | Winsness ............... C11B 1/02 554/8 |
| 2007/0244719 | A1 | 10/2007 | David |
| 2008/0061004 | A1 | 3/2008 | Balvanz |
| 2008/0154073 | A1 | 6/2008 | Petri et al. |
| 2009/0017164 | A1* | 1/2009 | Schisler ............... C12P 7/06 426/62 |
| 2010/0058649 | A1 | 3/2010 | Bootsma |
| 2010/0068649 | A1 | 3/2010 | Senzaki et al. |
| 2011/0086149 | A1 | 4/2011 | Bootsma |
| 2011/0275845 | A1* | 11/2011 | Woods ............... C11B 1/10 554/177 |
| 2013/0109873 | A1 | 5/2013 | Bootsma |
| 2014/0155639 | A1* | 6/2014 | Sticklen ............... C11B 13/00 494/23 |
| 2014/0242251 | A1* | 8/2014 | Bootsma ............... C12F 3/10 426/624 |
| 2015/0037857 | A1 | 2/2015 | Redford |

FOREIGN PATENT DOCUMENTS

| | | |
|---|---|---|
| GB | 1 247 473 | 9/1971 |
| WO | WO-03/016441 | 2/2003 |
| WO | WO-2004/057008 | 7/2004 |
| WO | WO-2004/081193 | 9/2004 |
| WO | WO-2004/113435 | 12/2004 |
| WO | WO-2008/039859 | 4/2008 |
| WO | WO-2008/082106 A1 | 7/2008 |
| WO | WO-2008/082108 | 7/2008 |
| WO | WO-2013/126561 A1 | 8/2013 |

OTHER PUBLICATIONS

Blanch et al., "Comprimidos de Accion Sostenida de Matriz Plastica," IT Farmaco—Ed. Pr., 1968, 23(4):183-194.

Bromberg, "Blends and Semi interpenetrating Networks of Zein and Poly(N,N-dimethylacrylamide)," J. Phys. Chem., vol. 100, No. 32, pp. 13811-13814 (1996).

Demirci et al., "Repeated-batch fermentation in biofilm reactors with plastic-composite supports for lactic acid production," Appl. Microbiol. Biotechnol., vol. 43, pp. 585-589 (1995).

Foreign Search Report dated Oct. 28, 2011 in related PCT Patent Application No. PCT/US2011/050705.

Friedrich et al.,"Properties and Processing of Corn Oils Obtained by Extraction with Supercritical Carbon Dioxide," JACOS, (1984), 61(12):1849-1851.

Friedrich et al. "Properties and Processing of Corn Oils Obtained by Extraction with Superficial Carbon Dioxide" 1984. JACOS. vol. 61 No. 12. pp. 1849-1851.

Friedrich et al., Properties and Processing of Corn Oil Obtained by Extraction with Supercritical Carbon Dioxide,: JACOS., (1984), 6(12):1849-1851.

Ikada et al., "Grafting of Proteins Onto Polymer Surfaces with the Use of Oxidized Starch," J. Biomed. Mater. Res., 13(4):607-22 (1979).

Kunduru et al., "Continuous ethanol production by *Zymomonas mobilis* and *Saccharomyces cerevisiae* in biofilm reactors," Journal of Industrial Microbiology, vol. 16, pp. 249-256 (1996).

Moreau et al., "The Composition of Crude Corn Oil Recovered after Fermentation via Centrifugation from a Commercial Dry Grind Ethanol Process", Journal of the American Oil Chemists' Society, 2010, 87(8):895-902.

Non-Final Office Action for U.S. Appl. No. 14/139,671 dated Jan. 13, 2016. 15 pages.

Non-Final Office Action on U.S. Appl. No. 15/631,420 dated Jan. 25, 2019.

Notice of Allowance dated May 12, 2015; U.S. Appl. No. 14/139,671.

Notice of Allowance on U.S. Appl. No. 15/631,420 dated Aug. 6, 2019.

Notice of Allowance on U.S. Appl. No. 15/631,420 dated Oct. 7, 2019.

PCT International Preliminary Report on Patentability dated Mar. 12, 2013 in related PCT Patent Application No. PCT/US2011/050705.

Shewry et al., "The Prolamin Storage Proteins of Sorghum and Millets," Rothamsted Research, Harpenden. Herts AL5 27Q, UK, Date Unknown.

Shin et al., "Preparation of Plastic and Biopolymer Multilayer Films by Plasma Source Ion Implementation," J. Agric. Food Chem., vol. 50, No. 16, pp. 4608-4614 (2002).

U.S. Office Action dated Aug. 1, 2012 in related U.S. Appl. No. 12/208,127.

(56) References Cited

OTHER PUBLICATIONS

U.S. Final Office Action dated Jul. 29, 2016 in U.S. Appl. No. 14/139,671.
U.S. Notice of Allowance for U.S. Appl. No. 12/208,127, dated Dec. 11, 2013 (1450).
U.S. Notice of Allowance dated Feb. 26, 2015.
U.S. Notice of Allowance dated May 12, 2015.
U.S. Notice of Allowance dated Sep. 2, 2015.
U.S. Notice of Allowance on U.S. Appl. No. 14/139,671 dated Nov. 28, 2016.
U.S. Office Action dated Feb. 12, 2013 in related U.S. Appl. No. 12/877,987.
U.S. Office Action dated Feb. 25, 2013 in related U.S. Appl. No. 13/656,490.
U.S. Office Action dated Mar. 31, 2014 in related U.S. Appl. No. 12/877,987.
U.S. Office Action dated May 22, 2013 in related U.S. Appl. No. 12/208,127.
U.S. Office Action dated May 7, 2014 in related U.S. Appl. No. 13/656,490.
U.S. Office Action dated Oct. 11, 2013 in related U.S. Appl. No. 13/656,490.
U.S. Office Action dated Oct. 15, 2014 in U.S. Appl. No. 14/139,671.
U.S. Office Action dated Oct. 8, 2014 in U.S. Appl. No. 12/877,987.
U.S. Office Action dated Jun. 21, 2012.
U.S. Office Action dated Jan. 28, 2015.
U.S. Office Action dated Sep. 9, 2015.
U.S. Office Action dated Nov. 25, 2011.
U.S. Office Action dated Aug. 1, 2012.
U.S. Office Action on U.S. Appl. No. 13/656,490 dated Apr. 18, 2016.
U.S. Office Action, U.S. Appl. No. 13/656,490, 10 pages (dated Jan. 27, 2017).
U.S. Office Action, U.S. Appl. No. 14/747,948, 7 pages (dated Dec. 29, 2016).
Winkler-Moser et al., "Antioxidant Activity of Phytochemicals from Distillers Dried Grain Oil", Journal of the American Oil Chemists' Society, 2009, 86(11):1073-1082.
Wu et al., "Chemical modification of zein by bifunctional polycaprolactone (PCL)," Polymer, vol. 44, pp. 3909-3919 (2003).
Wu et al., "Studies on the toughness and water resistance of zein-based polymers by modification," Polymer, vol. 44, pp. 3901-3908 (2003).
Yamada et al., "Improved water resistance in edible zein films and composites for biodegradable food packaging," International Journal of Food Science and Technology, vol. 30, pp. 599-608 (1995).
List, G.R. et al., "Properties and Processing of Corn Oils Obtained by Extraction with Supercritical Carbon Dioxide," JAOCS, vol. 61, No. 12, pp. 1849 (Dec. 1984).

\* cited by examiner

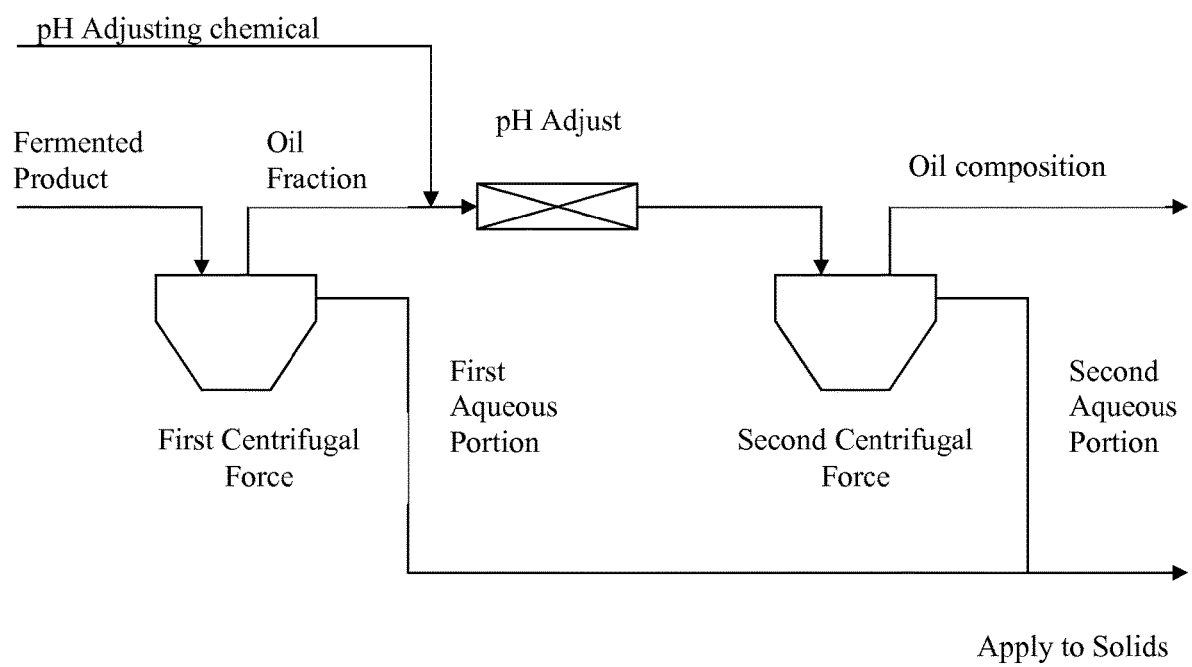

OIL COMPOSITION AND METHOD OF RECOVERING SAME

CROSS-REFERENCE TO RELATED APPLICATIONS

This application is a continuation of U.S. patent application Ser. No. 15/631,420, filed Jun. 23, 2017, which is a continuation of U.S. patent application Ser. No. 14/139,671, filed Dec. 23, 2013, now U.S. Pat. No. 9,695,449, which is a divisional of U.S. patent application Ser. No. 12/208,127, filed Sep. 10, 2008, now U.S. Pat. No. 8,702,819, the entire contents of which are incorporated herein by reference.

FIELD OF THE INVENTION

The present invention generally relates to oil compositions and methods of producing such oil compositions. More particularly, the present invention relates to an oil composition recovered from a fermentation product as well as methods of recovering such oil compositions for use in bio-diesel production and edible applications.

BACKGROUND OF THE INVENTION

Demand for alternative fuels, such as bio-diesel, has increased the need for sources of ethanol. Over the past few years, a renewed interest to further develop processes to manufacture ethanol from raw starch fermentation of various biomass sources such as corn (maize) has emerged. Research and development in this arena has spawned investigation as to the ways to boost profits by focusing on the commercial value of oil-containing byproducts produced during fermentation (hereinafter referred to as "fermentation products"). As a result of these investigations, various processes have emerged that focus on recovering oil product from these valuable by fermentation products.

Various processes for recovering oil from a fermentation product are currently known in the art. Such processes, however, can be expensive, inefficient or even dangerous. For example, some process, such as that set forth in WO 2008/039859, utilize a solvent extraction technique that, in turn, requires the use of volatile organic compounds such as hexane. Other processes, such as that set forth in U.S. Application Publication No. 2007/0238891, utilize high amounts of heat. Still other conventional processes, such as that set forth in U.S. Application Publication No. 2006/0041152 and 2006/0041153, simply apply a centrifugal force to a fermented product in an attempt to separate an oil product.

Conventional processes for recovering oil from a fermentation product can sacrifice oil quality such that the oil contains a high level of free fatty acids. The presence of a high level of free fatty acids can hamper the production of end products such as, for example, the yield and quality of any bio-diesel eventually produced with the oil as a feedstock. Processes for producing ethanol, such as the process set forth in WO 2004/081193, produce fermentation byproducts which contain increased levels of oils while maintaining a low level of free fatty acids. However, upon application of a centrifugal force to the fermented product, an emulsion can form which effectively locks the valuable oil within the emulsion. Thus, a problem exists in that both conventional and novel processes, alike, cannot effectively, efficiently or safely separate or "break" quality oil from a fermented product.

SUMMARY OF THE INVENTION

An oil composition is provided comprising a free fatty acid content of no greater than 5% w/w based on the total weight of the oil composition. The free fatty acid content can comprise at least one fatty acid selected from the group consisting of C16 palmitic, C18 stearic, C18-1 oleic, C18-2 linoleic, and C18-3 linolenic. In one embodiment, the oil composition has an iodine value of not greater than 125. In one embodiment, the oil composition has a combined moisture and insoluble content of no greater than 1% w/w based on the total weight of the oil composition. The oil composition is also relatively low in unsaponifiables. The oil composition is particularly suited for conversion into bio-diesel as well as useful in food grade, edible applications.

A method of recovering the oil composition from a fermentation process is also provided. The method can comprise the steps of fermenting a starch composition to form a fermented product. In one embodiment, the method comprises the step of separating an oil fraction from the fermented product, wherein the oil fraction contains the oil composition. In one embodiment, the method comprises the step of adjusting the pH of the oil fraction. In one embodiment, the method comprises the step of recovering the oil composition from the pH adjusted oil fraction. The recovered oil composition may comprise any of the same components as those described above, alone or in any combination.

The fermentation process, in one embodiment, may comprise a conventional enzymatic liquefaction process carried out as a multi-step hot slurry process (e.g., with cooking). In another embodiment, the fermentation process relies primarily on an enzymatic process without the addition of heat (i.e., without cooking). In one embodiment, the starch composition is saccharified with an enzyme composition followed by fermenting the starch composition to yield a fermented product. In one embodiment, the saccharifying and fermenting steps may be carried out simultaneously in one reaction vessel. In an alternative embodiment, the saccharifying and fermenting steps may be carried out sequentially in separate reaction vessels. The step of fermenting the starch composition can be carried out in the presence of a microorganism. In one embodiment, the microorganism is a yeast such as, for example, *Saccharomyces* spp. In one embodiment, *Saccharomyces* spp is *S. cerevisiae* or *S. uvarum*. In one embodiment, the microorganism is a bacteria.

In on embodiment, the enzyme composition comprises acid alpha-amylase and glucoamylase. In one embodiment, the alpha-amylase and glucoamylase is included at an activity ratio of at least 0.35 AFAU/AGU to produce dextrins and glucose. In another embodiment, the acid alpha-amylase is present in an amount of 10-10000 AFAU/kg of dried solids. In one embodiment, the acid alpha-amylase is present in an amount of 500-2500 AFAU/kg of dried solids. In another embodiment, the acid alpha-amylase is present in an amount of 100-1000 AFAU/kg of dried solids.

In one embodiment, the acid alpha-amylase and glucoamylase is included at an activity ratio of at least 0.40. In another embodiment, the acid alpha-amylase and glucoamylase is included at an activity ratio of at least 0.50. In one embodiment, the starch composition is hydrolyzed at a pH of 4.0 to 5.0. In one embodiment, the fermentation is carried out at a temperature of between 10° C. and 35° C. In one embodiment, the starch composition that is saccharified is in a slurry comprising water and 5% to 60% dried solids. In one embodiment, the starch composition is held at a temperature of 0° C. to 20° C. below initial gelatinization temperature of the starch composition for a period of 5 minutes to 12 hours during saccharifying and before fermenting.

The starch composition can be obtained from corn, cobs, wheat, barley, rye, milo, sago, cassava, manioc, tapioca, sorghum, rice or potatoes. The fermented product can be a variety of fermentation byproducts such as, for example, beer, whole stillage, thin stillage or syrup.

The fermented product's composition may vary according to the source of starch. In one embodiment, the fermented product comprises from 60% to 95% moisture. In one embodiment, the fermented product comprises from 5% to 30% protein. In one embodiment, the fermented product comprises from 5% to 40% oil. In one embodiment, the remainder of the fermented product comprises starch, neutral detergent fiber or a combination thereof.

The step of separating an oil fraction from the fermented product can be accomplished by applying a first centrifugal force to the oil fraction. The first centrifugal force may form an emulsion. The centrifugal force can be applied via a separator or centrifuge. The separator or centrifuge can be a press, extruder, a decanter centrifuge, a disk stack centrifuge, a disk nozzle centrifuge, a screen centrifuge or a combination thereof.

The separated oil fraction may comprise from 10% to 60% moisture in one embodiment, In one embodiment, the separated oil fraction may comprise from 10% to 40% protein. The actual amount of oil within the separated oil fraction may vary. For example, in one embodiment, the oil fraction may comprise from 20% w/w to 70% w/w oil by weight. In another embodiment, the oil fraction may comprise from 30% w/w to 60% w/w oil by weight. In yet another embodiment, the oil fraction may comprise from 40% w/w to 50% w/w oil by weight. In one embodiment, the remainder of the separated oil fraction may comprise may comprise starch, neutral detergent fiber or a combination thereof.

The method may further comprise the step of removing a first aqueous portion after separating the oil fraction from the fermented product. The composition of the first aqueous portion may vary. For example, in one embodiment, the first aqueous portion comprises from 65% to 95% moisture. In one embodiment, the first aqueous portion comprises from 12% to 40% protein. In one embodiment, the first aqueous portion comprises from up to 10% oil. In one embodiment, the remainder of the first aqueous portion comprises starch, neutral detergent fiber or a combination thereof.

The method further comprises the step of adjusting the pH of the oil fraction. By adjusting the pH, the pH may be raised or lowered. In one embodiment, the pH is adjusted to a range of from 7 to 10. In another embodiment, the pH is adjusted to a range of from 7.5 to 9. In yet another embodiment, the pH is adjusted to a range of from 8.0 to 8.5. The pH can be adjusted by introducing an inorganic base such as, for example, KOH or NaOH. In another embodiment, the pH can be adjusted by introducing an organic base such as, for example, ammonia or urea.

In one embodiment, the pH is adjusted by about 0.1% to about 99% of the original pH the oil fraction. In another embodiment, the pH is adjusted by about 20% to about 80% of the original pH the oil fraction. In yet another embodiment, the pH is adjusted by about 45% to about 65% of the original pH the oil fraction.

In one embodiment, the pH is adjusted upward by at least 0.1 pH units. In another embodiment, the pH is adjust upward by at least 0.2 pH units. In yet another embodiment, the pH is adjusted upward by at least 0.3 pH units.

The method may further comprise the step of applying a second centrifugal force to the oil fraction after adjusting the pH. The second centrifugal force can be applied via a separator or centrifuge. The separator or centrifuge can be a press, extruder, a decanter centrifuge, a disk stack centrifuge, a screen centrifuge or a combination thereof.

The method may further comprise the step of removing a second aqueous portion after applying the second centrifugal force. The composition of the second aqueous portion may vary. In one embodiment, the second aqueous portion comprises from 60% to 80% moisture. In one embodiment, the second aqueous portion comprises from 10% to 40% protein. In one embodiment, the second aqueous portion comprises up to 50% oil. In one embodiment, the remainder of the second aqueous portion comprises starch, neutral detergent fiber or a combination thereof. The second aqueous portion can be used to treat distillers' dried grain or other solids where an increased level of these components is desirable.

The method further comprises the step of recovering the oil composition from the pH adjusted oil fraction. The oil composition may vary. In one embodiment, the recovered oil composition comprises no greater than about 2% moisture. In one embodiment, the recovered oil composition comprises from about 80% to about 100% oil. In one embodiment, the recovered oil composition comprises a free fatty acid content of no greater than 5%. In one embodiment, the remainder of the recovered oil composition comprises protein, starch, neutral detergent fiber or a combination thereof.

Various articles of manufacture may comprise the oil composition described herein. Suitable examples include various oleochemicals, feeds or oils suitable for human consumption. In one embodiment, the oleochemical is a feedstock chemical suitable for fatty acid methyl ester (e.g., bio-diesel) production and fatty acid ethyl ester production. Other exemplary articles include, but are not limited to, soap, detergent, wire insulation, industrial lubricant, leather treatment, cutting oil, mining agent for oil well drilling, ink removal, plastic stabilizer, ink production component, rubber production component, wax, shampoo, personal hygiene component, or a food emulsifier. The oil composition may also be suitable for an edible oil, a carrier for drug molecules in pharmaceutical preparations, a health food component or supplement, or dietary supplement.

A fuel composition comprising the oil composition is provided, In one embodiment of the fuel composition, the oil composition comprises a free fatty acid content of no greater than 5% w/w based on the total weight of the composition. A fuel additive comprising the oil composition is also provided. In one embodiment of the fuel additive, the oil composition comprises a free fatty acid content of no greater than 5% w/w based on the total weight of the composition.

DESCRIPTION OF THE DRAWINGS

FIG. 1 is a process flow diagram of one embodiment of a method of recovering an oil composition.

DETAILED DESCRIPTION OF THE EMBODIMENTS

The present invention generally relates to oil compositions recovered from a fermentation byproduct. The oil compositions contain low levels of free fatty acids making them valuable for use in bio-diesel, edible and nutraceutical applications. The present invention also relates to methods of recovering such oil compositions from a fermentation process. These methods overcome the oil separation challenges associated with both novel and conventional methods by adjusting the pH of the resulting oil fraction to break or free the oil for recovery.

The recovered oil composition can contain low levels of moisture, insolubles and unsaponifiables (MIU content). Moisture, as contemplated herein, includes water and any volatile material such as, for example, hexane, ethanol, methanol or a combination thereof. Insoluble matter (i.e., "insolubles"), as contemplated herein, refers to and includes any matter incapable of being dissolved in the aqueous portion, oil fraction or oil composition. Unsaponifiable matter (i.e., "unsaponifiables") includes any variety of possible non-triglyceride materials that act as contaminants during bio-diesel production. Unsaponifiable matter can significantly reduce the end product yields of the oil composition and can, in turn, reduce end product yields of processes such as, for example, bio-diesel production processes.

Maintaining low levels of moisture is especially desirable because moisture fosters the formation of free fatty acids instead of esters. In one embodiment, the oil composition contains no greater than 1% w/w of moisture and insolubles, combined, based on the total weight of the oil composition. Preferably, the oil composition contains no greater than 0.5% w/w of combined moisture and insolubles. Most preferably, the oil composition contains not greater than 0.1% w/w of combined moisture and insolubles.

In one embodiment, the oil composition comprises no greater than 3% w/w of unsaponifiables, based on the total weight of the oil composition. Preferably, the oil composition comprises no greater than 2% w/w of unsaponifiables. Most preferably, the oil composition comprises no greater than 1% w/w of unsaponifiables.

In one embodiment, the oil composition contains no greater than 1% w/w of total moisture content, alone, based on the total weight of the oil composition. Preferably, the moisture content, alone, is no greater than 0.5% w/w. Most preferably, the moisture content, alone, is no greater than 0.1% w/w.

In one embodiment, the oil composition contains no greater than 1% w/w insolubles, alone, based on the total weight of the oil composition. Preferably, the insolubles content, alone, is no greater than 0.5% w/w. Most preferably, the insolubles content, alone, is no greater than 0.1% w/w.

The oil composition exhibits an iodine value acceptable for bio-diesel production and, preferably, exhibits an iodine value lower than that expected from a neat oil sample. The iodine value is determined by measuring the number of double bonds in the mixture of fatty acid chains in the composition by introducing iodine into 100 grams of the sample under test conditions and measuring how many grams of that iodine are absorbed. Iodine absorption occurs at double bond positions so a higher number indicates a higher quantity of double bonds in the composition. The oil composition has an iodine value of no greater than about 125 in one embodiment. In another embodiment, the iodine value is no greater than about 117.5. In yet another embodiment, the iodine value is no greater than about 110.

The fuel properties of the bio-diesel are determined by the amounts of each fatty acid in the feedstock used to produce the fatty acid methyl esters. The oil composition described herein has a free fatty acid content level that can reduce the amount of front-end refining or processing for use in bio-diesel production. In one embodiment, the oil composition comprises a free fatty acid content that is no greater than 15% w/w of the entire oil composition. Preferably, the free fatty acid content is no greater than 5% w/w. Most preferably, the free fatty acid is no greater than 2% w/w.

The free fatty acid content of the oil composition is comprised of various fatty acids known in the art. In one embodiment, the oil composition comprises C16 palmitic acid which represents no greater than 15% w/w of the total fatty acid content, based on the total weight of the oil composition. In another embodiment, the C16 palmitic acid content is no greater than 12.5% w/w of the total fatty acid content. In yet another embodiment, the C16 palmitic acid content is no greater than 10% w/w of the total fatty acid content.

In one embodiment, the oil composition comprises C18 stearic acid which represents no greater than 3% w/w of the total fatty acid content, based on the total weight of the oil composition. In another embodiment, the C18 stearic acid content is no greater than 2.25% w/w of the total fatty acid content. In yet another embodiment, the C18 stearic acid content is no greater than 1.5% w/w of the total fatty acid content.

In one embodiment, the oil composition comprises C18-1 oleic acid which represents no greater than 30% w/w of the total fatty acid content, based on the total weight of the oil composition. In another embodiment, the C18-1 oleic acid content is no greater than 27.5% w/w of the total fatty acid content. In yet another embodiment, the C18-1 oleic acid content is no greater than 25% w/w of the total fatty acid content.

In one embodiment, the oil composition comprises C18-2 linoleic acid which represents no greater than 60% w/w of the total fatty acid content, based on the total weight of the oil composition. In another embodiment, the C18-2 linoleic acid content is no greater than 55% w/w of the total fatty acid content. In yet another embodiment, the C18-2 linoleic acid content is no greater than 50% w/w of the total fatty acid content.

In one embodiment, the oil composition comprises C18-3 linolenic acid which represents no greater than 1.5% w/w of the total fatty acid content, based on the total weight of the oil composition. In another embodiment, the C18-3 linolenic acid content is no greater than 1.0% w/w of the total fatty acid content. In yet another embodiment, the C18-3 linolenic acid content is no greater than 0.5% w/w of the total fatty acid content.

The oil composition can further comprise various carotene, carotenoid and antioxidant or neutraceutical compounds. In one embodiment, the oil composition contains a lutein content of at least 50 mcg/g. In another embodiment, the lutein content is at least 75 mcg/g. In yet another embodiment, the lutein content is at least 100 mcg/g.

In one embodiment, the oil composition contains a zeaxanthin content of at least 30 mcg/g. In another embodiment, the zeaxanthin content is at least 65 mcg/g. In yet another embodiment, the zeaxanthin content is at least 100 mcg/g.

In one embodiment, the oil composition contains a cis-lutein/zeaxanthin content of at least 10 mcg/g. In another embodiment, the cis-lutein/zeaxanthin content is at least 30 mcg/g. In yet another embodiment, the cis-lutein/zeaxanthin content is at least 50 mcg/g.

In one embodiment, the oil composition contains an alpha-cryptoxanthin content of at least 5 mcg/g. In another embodiment, the alpha-cryptoxanthin content is at least 7.5 mcg/g. In yet another embodiment, the alpha-cryptoxanthin content is at least 10 mcg/g.

In one embodiment, the oil composition contains a beta-cryptoxanthin content of at least 5 mcg/g. In another embodiment, the beta-cryptoxanthin content is at least 27.5 mcg/g. In yet another embodiment, the beta-cryptoxanthin content is at least 50 mcg/g.

In one embodiment, the oil composition contains an alpha-carotene content of at least 0.5 mcg/g. In another embodiment, the alpha-carotene content is at least 1.25 mcg/g. In yet another embodiment, the alpha-carotene content is at least 2 mcg/g.

In one embodiment, the oil composition contains a beta-carotene content of at least 1 mcg/g. In another embodiment, the beta-carotene content is at least 2 mcg/g. In yet another embodiment, the beta-carotene content is at least 3 mcg/g.

In one embodiment, the oil composition contains a cis-beta-carotene content of at least 0.1 mcg/g. In another embodiment, the cis-beta-carotene content is at least 0.5 mcg/g. In yet another embodiment, the cis-beta-carotene content is at least 1 mcg/g.

In one embodiment, the oil composition contains an alpha-tocopherol content of at least 50 mcg/g. In another embodiment, the alpha-tocopherol content is at least 125 mcg/g. In yet another embodiment, the alpha-tocopherol content is at least 200 mcg/g.

In one embodiment, the oil composition contains a beta-tocopherol content of at least 2 mcg/g. In another embodiment, the beta-tocopherol content is at least 3.5 mcg/g. In yet another embodiment, the beta-tocopherol content is at least 5 mcg/g.

In one embodiment, the oil composition contains a gamma-tocopherol content of at least 300 mcg/g. In another embodiment, the gamma-tocopherol content is at least 650 mcg/g. In yet another embodiment, the gamma-tocopherol content is at least 1000 mcg/g.

In one embodiment, the oil composition contains a delta-tocopherol content of at least 15 mcg/g. In another embodiment, the delta-tocopherol content is at least 45 mcg/g. In yet another embodiment, the delta-tocopherol content is at least 75 mcg/g.

In one embodiment, the oil composition contains an alpha-tocotrienol content of at least 50 mcg/g. In another embodiment, the alpha-tocotrienol content is at least 125 mcg/g. In yet another embodiment, the alpha-tocotrienol content is at least 200 mcg/g.

In one embodiment, the oil composition contains a beta-tocotrienol content of at least 5 mcg/g. In another embodiment, the beta-tocotrienol content is at least 12.5 mcg/g. In yet another embodiment, the beta-tocotrienol content is at least 20 mcg/g.

In one embodiment, the oil composition contains a gamma-tocotrienol content of at least 80 mcg/g. In another embodiment, the gamma-tocotrienol content is at least 290 mcg/g. In yet another embodiment, the gamma-tocotrienol content is at least 500 mcg/g.

In one embodiment, the oil composition contains a delta-tocotrienol content of at least 5 mcg/g. In another embodiment, the delta-tocotrienol content is at least 12.5 mcg/g. In yet another embodiment, the delta-tocotrienol content is at least 20 mcg/g.

The oil composition can be used in a wide variety of applications. Such exemplary applications include the areas of oleochemicals, feed (e.g., animal feed) as well as oils suitable for human consumption. Oleochemicals include feedstock chemicals that are suitable for bio-diesel production (fatty acid methyl esters). Industrial oleochemicals are useful in the production of soaps, detergents, wire insulation, industrial lubricants, leather treatments, cutting oils, mining agents for oil well drilling, ink removal, plastic stabilizers, ink and in rubber production. Other industrial applications include waxes, shampoos, personal hygiene and food emulsifier or additive products.

Products fit for human consumption include edible oils that meet GRAS crude oil standards, as well as carriers for drug molecules in pharmaceutical preparations. These products fits for human consumption further include nutraceutical applications. The oil compositions described herein contain higher than average levels of various nutraceuticals such as, for example, tocopherols, tocotrienols and phytosterols. In one embodiment and while not intending to be bound to one particular theory, the oil composition's higher than average levels of various nutraceuticals can be attributable to the removal of corn oil directly form the whole kernel as opposed to simply the corn germ itself. The nutraceuticals in the present oil composition may be further processed for inclusion in various applications such as health foods, dietary supplements, food supplements, and food fortification products.

The present invention also provides a method of recovering an oil composition from a fermentation process. A process flow diagram of one embodiment of the inventive method is shown in FIG. 1. In one embodiment, the method includes the step of fermenting a starch composition to form a fermented product. In another embodiment, the method includes the step of separating an oil fraction from the fermented product, wherein the oil fraction contains the oil composition. In yet another embodiment, the method includes the step of adjusting the pH of the oil fraction. In another embodiment, the method includes the step of recovering the oil composition from the pH adjusted oil fraction.

Various fermentation processes are suitable for producing a fermented product as set forth in the present method. Suitable fermentation processes include, for example, those that convert various starch-containing plant materials to various alcohols. In a preferred embodiment, the fermentation process is a raw starch fermentation process capable of producing high levels of alcohol during fermentation of plant material as well as high alcohol beer. In one embodiment, the alcohol product is ethanol.

In one embodiment, the fermentation process is a conventional enzymatic liquefaction process. In one embodiment of such a process, a starch slurry is heated to between 50° C. to 100° C. (i.e., cooked). In a preferred embodiment, the starch slurry is heated to between 60° C. to 90° C. In a particularly preferred embodiment, the starch slurry is head to between 80° C. and 85° C. Next, a thermostable alpha-amylase is added to initiate liquefaction.

In one embodiment, the slurry can then be jet-cooked at a temperature between 100° C. to 145° C. to complete gelatinization of the slurry. In a preferred embodiment, the slurry can then be jet-cooked at a temperature between 102° C. to 135° C. to complete gelatinization. In a particularly preferred embodiment, the slurry can then be jet-cooked at a temperature between 105° C. to 125° C. to complete gelatinization of the slurry.

In one embodiment, the slurry can be cooled to a temperature between 50° C. to 100° C. In a preferred embodiment, the slurry can be cooled to a temperature between 65° C. to 97° C. In a particularly preferred embodiment, the slurry can be cooled to a temperature between 60° C. to 95° C. Next, an additional alpha-amylase can be added to finalize hydrolysis. The liquefaction process can be generally carried out at a pH of between about 3 and about 8. Preferably, the liquefaction process is generally carried out at a pH of between about 4 and about 7. In a particularly preferred embodiment, the liquefaction process can be generally carried out at a pH of between about 5 and about 6.

In one embodiment of the conventional enzymatic liquefaction process, the dextrins from the liquefaction are further hydrolyzed to produce low molecular sugars DP1-3 that can be metabolized by yeast. The hydrolysis is typically accomplished using glucoamylases, alternatively or in addition to glucoamylases, alpha-glucosidases and/or acid alpha-amylases can be used. A full saccharification step can last up to 72 hours. In an alternative embodiment, a pre-saccharification step lasting 40-90 minutes at a temperature above 50° C. is followed by a complete saccharification via a process known as simultaneous saccharification and fermentation (SSF). In one embodiment of the conventional enzymatic liquefaction process, fermentation may be performed using a yeast, e.g., from *Saccharomyces* spp., which is added to the milled and liquefied whole grains (e.g., mash).

In another embodiment, the fermentation process is carried out without creating a hot slurry (i.e., without cooking). In such an embodiment, the fermentation process includes the step of saccharifying the starch composition with an enzyme composition to form a saccharified composition (e.g., without cooking). In one embodiment the starch composition comprises water and from 5% to 60% dried solids granular starch, based on the total weight of the starch composition. In another embodiment, the starch composition comprises 10% to 50% dried solids granular starch, based on the total weight of the starch composition. In a preferred embodiment, the starch composition comprises 15% to 40% dried solids, based on the total weight of the starch composition. In a particularly preferred embodiment, the starch composition comprises about 20% to 25% dried solids granular starch, based on the total weight of the starch composition. The granular starch can be obtained from various sources such as, for example, plant materials. Suitable plant materials include, but are not limited to, for example, tubers, roots, stems, cobs, legumes, cereals or whole grain. In one embodiment, the granular starch can be obtained from, for example, corns, cobs, wheat, barley, rye, milo, sago, cassava, tapioca, sorghum, rice, peas, bean, banana or potatoes.

In one embodiment, the raw material comprising the starch is milled in order to open up the structure and allowing for further processing. Dry milling as well as wet milling may be used. When wet milling is applied, the steps of soaking or steeping step may precede milling. Both dry and wet milling is well known in the art of alcohol manufacturing and is preferred for the fermentation process described herein.

In one embodiment, the enzyme composition comprises an acid alpha-amylase. Any suitable acid alpha-amylase may be used in the present method. In one embodiment, the acid alpha-amylase is an acid bacterial alpha-amylase or an acid fungal alpha-amylase or a variant of an acid alpha-amylase or a combination thereof. The acid alpha-amylase can be derived from a bacterial or a fungal source or a combination thereof. In one embodiment, the acid fungal alpha-amylase is obtained from a strain of *Aspergillus*, preferably a strain of *Aspergillus niger* or a strain of a strain of *Aspergillus oryzae*. In another embodiment, the acid alpha-amylase for use in the present invention may be derived from a strain of *B. licheniformis*, *B. amyloliquefaciens*, and *B. stearothermophilus*.

In one embodiment, the enzyme composition comprises a glucoamylase. The may glucoamylase can be derived from a microorganism or a plant. In one embodiment, the glucoamylase is of fungal origin such as *Aspergillus* glucoamylases, in particular *A. niger* G1 or G2 glucoamylase. In another embodiment, the glucoamylase is derived from *A. awamori* glucoamylase, *A. oryzae*, or variants or fragments thereof. In yet another embodiment, the glucoamylase include the glucoamylases derived from *Aspergillus niger*. In another embodiment, the glucoamylase is derived from *Aspergillus oryzae*. Other suitable glucoamylases include *Talaromyces* glucoamylases, in particular derived from *Talaromyces emersonii*, *Talaromyces leycettanus*, *Talaromyces duponti*, *Talaromyces thermophilus*, *Clostridium*, in particular *C. thermoamylolyticum* and *C. thermohydrosulfuricum*.

In one embodiment, the enzyme composition comprises at least one additional enzyme selected from the group consisting of xylanases, cellulases and phytases. A xylanase used according to the invention may be derived from any suitable organism, including fungal and bacterial organisms, such as *Aspergillus*, *Disporotrichum*, *Penicillium*, *Neurospora*, *Fusarium* and *Trichoderma*. The cellulase activity may be a cellulase of microbial origin, such as derivable from a strain of a filamentous fungus (e.g., *Aspergillus*, *Trichoderma*, *Humicola*, *Fusarium*). A phytase used according to the invention may be any enzyme capable of effecting the liberation of inorganic phosphate from phytic acid (myo-inositol hexakisphosphate) or from any salt thereof (phytates). In yet another embodiment, the enzyme composition may comprise a debranching enzyme, such as an isoamylase or a pullulanases. Isoamylase hydrolyses alpha-1,6-D-glucosidic branch linkages in amylopectin and beta-limit dextrins and can be distinguished from pullulanases by the inability of isoamylase to attack pullulan, and by the limited action on alpha-limit dextrins. Debranching enzyme may be added in effective amounts well known to the person skilled in the art.

In one embodiment, an additional enzyme is preferably added together with the acid alpha-amylase and the glucoamylase. In one embodiment, the additional enzyme is xylanase. In one embodiment, xylanase may be added in amounts of 1-50000 FXU/kg dried solids. In another embodiment, xylanase may be added in amounts of 5-5000 FXU/kg dried solids. In a preferred embodiment, xylanase may be added in amounts of 10-500 FXU/kg dried solids.

In one embodiment, cellulases may be added in the amounts of 0.01-500000 EGU/kg dried solids. In another embodiment, cellulases may be added in the amounts of 0.1-10000 EGU/kg dried solids. In yet another embodiment, cellulases may be added in the amounts of 1-5000 EGU/kg dried solids. In a preferred embodiment, cellulases may be added in the amounts of 10-500 EGU/kg dried solids. In a particularly preferred embodiment, cellulases may be added in the amounts of 100-250 EGU/kg dried solids.

In one embodiment, phytase may be in the range of 0.5-250000 FYT/kg dried solids. In another embodiment, phytase may be in the range of 1-100000 FYT/kg dried solids. In yet another embodiment, phytase may be in the range of 5-25000 FYT/kg dried solids. In a preferred embodiment, phytase may be in the range of 10-10000 FYT/kg. In a particularly preferred embodiment, phytase may be in the range of 100-1000 FYT/kg dried solids.

In one embodiment, the steps of saccharifying the starch composition and fermenting the saccharified composition are performed in a sequential manner in a shared reaction vessel. The temperature is below the initial gelatinization temperature of the particular granular starch to be processed. In such an embodiment, the step of saccharifying the starch composition is carried out at a temperature of between 10° C. and 35° C. In a preferred embodiment, the step of saccharifying the starch composition is carried out at a temperature of between 29° C. and 35° C. In a particularly preferred embodiment, the step of saccharifying the starch composition is carried out at a temperature of between 30° C. and 34° C., such as around 32° C.

In one embodiment where the steps of saccharifying the starch composition and fermenting the saccharified composition are performed in a sequential manner in a shared reaction vessel, the starch composition can comprise a slurry that is held in contact with the acid alpha-amylase, the glucoamylase and the yeast for a period of time sufficient to allow saccharification or hydrolysis of the starch and fermentation of the released sugars. In one embodiment, the starch composition is held for a period of about 25 to about 190 hours, In another embodiment, the starch composition is held for about 30 to about 180 hours. In yet another embodiment, the starch composition is held for about 40 to about 170 hours. In another embodiment, the starch composition is held for about from 50 to about 160 hours. In yet another embodiment, the starch composition is held for about 60 to about 150 hours. In another embodiment, the starch composition is held for about 70 to about 140 hours. In yet another embodiment, the starch composition is held for about 80 to about 130 hours. In a preferred embodiment, the starch composition is held for about 85 to about 110 hours.

In an embodiment, the pH is in the range of about 3.0 to about 7.0. In another embodiment, the pH is in the range of about 3.5 to about 6.0. In yet another embodiment, the pH is in the range of about 4.0 to about 5.0. In another embodiment, the pH is in the range of about 4.3 to about 4.6.

In another embodiment, the steps of saccharifying the starch composition and fermenting the saccharified composition are performed sequentially in separate vessels. The temperature is below the initial gelatinization temperature of the particular granular starch to be processed. In such an embodiment, the step of saccharifying the starch composition is carried out at a temperature of between 5° C. and 50° C. In a preferred embodiment, the step of saccharifying the starch composition is carried out at a temperature of between 7° C. and 45° C. In a particularly preferred embodiment, the step of saccharifying the starch composition is carried out at a temperature of between 10° C. and 40° C.

In one embodiment, the starch composition comprises a slurry that is held in contact with the acid alpha-amylase and the glucoamylase. In one embodiment, the starch composition is held for about 10 to about 200 hours. In yet another embodiment, the starch composition is held for about 20 to about 150 hours. In a preferred embodiment, the starch composition is held for about 40 to about 100 hours.

In an embodiment, the pH of the saccharification step is in the range of about 1 to about 9. In another embodiment, the pH is in the range of about 2 to about 8. In yet another embodiment, the pH is in the range of about 3 to about 7.

In an embodiment where the step of fermenting the saccharified composition is performed sequentially in a separate vessel, the step of fermenting the saccharified composition is carried out at a temperature of between 5° C. and 75° C. In a preferred embodiment, the step of fermenting the saccharified composition is carried out at a temperature of between 6° C. and 70° C. In a particularly preferred embodiment, the step of fermenting the saccharified composition is carried out at a temperature of between 7° C. and 65° C.

In one embodiment, the step of fermenting the saccharified composition is held for about 10 to about 200 hours. In yet another embodiment, the step of fermenting the saccharified composition is held for about 20 to about 150 hours.

In a preferred embodiment, the step of fermenting the saccharified composition is held for about 40 to about 100 hours.

In an embodiment, the pH of the step of fermenting the saccharified composition is in the range of about 1 to about 10. In another embodiment, the pH is in the range of about 2 to about 9. In yet another embodiment, the pH is in the range of about 3 to about 8.

In either a single or dual vessel embodiment, the glucoamylase is added in an effective amount, which is a concentration of glucoamylase amylase sufficient for its intended purpose of degrading the dextrins resulting from the acid alpha-amylase treatment of the starch composition. In one embodiment, the glucoamylase activity is present in an amount of 20-200 AGU/kg of dried solids. In another embodiment, the glucoamylase activity is present in an amount of 100-1000 AGU/kg of dried solids. In a preferred embodiment, the glucoamylase activity is present in an amount of 200-400 AGU/kg of dried solids, such as 250 AGU/kg dried solids. When measured in AGI units, the glucoamylase activity can be present in an amount of 10-100000 AGI/kg of dried solids in one embodiment, In another embodiment, the glucoamylase activity is present in an amount of 50-50000 AGI/kg of dried solids. In a preferred embodiment, the glucoamylase activity is present in an amount of 100-10000 AGI/kg of dried solids. In a particularly preferred embodiment, the glucoamylase activity is present in an amount of 200-5000 AGI/kg of dried solids.

In either a single or dual vessel embodiment, the acid alpha-amylase is added in an effective amount, which is a concentration of acid alpha-amylase sufficient for its intended purpose of converting the granular starch in the starch composition to dextrins. In one embodiment, the acid alpha-amylase is present in an amount of 10-10000 AFAU/kg of dried solids. In another embodiment, the acid alpha-amylase is present in an amount of 500-2500 AFAU/kg of dried solids. In a preferred embodiment, the acid alpha-amylase is present in an amount of 100-1000 AFAU/kg of dried solid, such as, for example, approximately 500 AFAU/kg dried solids. When measured in AAU units, the acid alpha-amylase activity is present in an amount of 5-500000 AAU/kg of dried solids in one embodiment. In a preferred embodiment, the acid alpha-amylase is present in an amount of 500-50000 AAU/kg of dried solids. In a particularly preferred embodiment, the acid alpha-amylase is present in an amount of 100-10000 AAU/kg of dried solids, such as, for example, 500-1000 AAU/kg dried solids.

In one embodiment, the acid alpha-amylase is added in such a manner that, when added in an effective amount, has activity at a pH in the range of 3.0 to 7.0. In a preferred embodiment, the alpha-amylase has activity at a pH in the range of from 3.5 to 6.0. In a particularly preferred embodiment, the alpha-amylase has activity at a pH in the range of from 4.0-5.0.

In either a single or dual vessel embodiment, the activities of acid alpha-amylase and glucoamylase are present in a ratio of between 0.3 and 5.0 AFAU/AGU. In one embodiment, the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. In one embodiment, the ratio between acid alpha-amylase activity and glucoamylase activity is less than 4.5, less than 4.0, less than 3.5, less than 3.0, less than 2.5, or even less than 2.25 AFAU/AGU. In terms of AUU/AGI, the activities of acid alpha-amylase and glucoamylase may be present in a ratio of between 0.4 and 6.5 AUU/AGI. In a preferred embodiment, the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. In one embodiment, the ratio between acid alpha-amylase activity and glucoamylase activity is preferably less than 6.0, less than 5.5, less than 4.5, less than 4.0, less than 3.5, or even less than 3.0 AUU/AGI.

In one embodiment, the fermentation results in a beer composition that undergoes further processing to produce whole stillage. In either a cooking or non-cooking process, the whole stillage can comprise a variety of components including, but not limited to, solids and oil. In one embodiment, the whole stillage can be subjected to further processing steps such as, for example, decanting and centrifugation to produce thin stillage. A portion of the solids comprising the whole stillage may be processed to form a wet cake which is dried to form distillers' dried grain. In one embodiment, moisture can be removed from the thin stillage to create a concentrated fermented product (e.g., syrup). Moisture can be removed in a variety of ways such as, for example, through evaporation under vacuum which, in turn, can prevent fouling. In one embodiment, the fermented product comprises oil and solids which can be subjected to drying and applied to any distillers' dried grain separated from the whole stillage.

In one embodiment, the method comprises the step of separating an oil fraction from the fermented product, wherein the oil fraction contains an oil composition. In one embodiment, the step of separating the oil fraction is accomplished by applying a first centrifugal force to the fermented product to form an oil fraction. In one embodiment, the oil fraction comprises an oil-rich emulsion phase and an aqueous phase containing heavy components. In a preferred embodiment, a first centrifugal force is applied to the fermented product soon after initial production of the fermented product to maintain oil composition quality and prevent exposure to heat and oxygen. If the fermented product is left exposed for extended periods of time in the presence of moisture, hydrolysis of the oils may occur which leads to the formation of free fatty acids.

The first centrifugal force, in one embodiment, is applied via a separator or centrifuge or a combination thereof, including, but not limited to, for example, a press, extruder, a decanter centrifuge, a disk stack centrifuge, a screen centrifuge or a combination thereof. In one embodiment, a continuous flow at about 4000 g is maintained. One of ordinary skill in the art will appreciate that the speed or amount of centrifugal force applied will depend on various factors such as sample size and may be adjusted appropriately depending on such factors. Suitable separators and centrifuges are available from various manufacturers such as, for example, Seital of Vicenza, Italy, Westfalia of Oelde, Germany or Alfa Laval of Lund, Sweden.

In one embodiment, a centrifuge, alone, can be used to apply the centrifugal force to the fermented product. In one embodiment, back pressure is applied to the heavy phase of the resulting oil fraction to improve separation of the oil composition from the aqueous phase and heavy components. A back pressure can be applied by adjusting the centrifuge to restrict the flow of the oil fraction from the centrifuge.

In one embodiment, the resulting oil fraction contains from about 20% w/w to about 70% w/w oil. In another embodiment, the oil fraction contains from about 30% w/w to about 60% w/w oil. In yet another embodiment, the oil fraction contains from about 40% w/w to about 50% w/w oil. The oil fraction may also comprise varying amounts of the overall fermented product volume. In one embodiment, the oil fraction comprises about 20% w/w of the initial fermented product volume. In any of the aforementioned embodiments, the oil fraction can be an emulsion.

In one embodiment, the method further comprises the step of removing a first aqueous portion after separating the oil fraction from the fermented product. The first aqueous portion, in one embodiment, comprises about 65% to about 95% moisture, based on the total weight of the first aqueous portion. In one embodiment, the first aqueous portion comprises about 12% to about 40% protein, based on the total weight of the first aqueous portion. In one embodiment, the first aqueous portion comprises up to about 10% oil, based on the total weight of the first aqueous portion. In one embodiment, the remainder of the first aqueous portion comprises starch, neutral detergent fiber or a combination thereof. All or a fraction of the first aqueous portion may be further processed or applied to solids such as, for example, distillers' dried grain.

In one embodiment, the method further comprises the step of adjusting the pH of the oil fraction to a level that separates or breaks the oil fraction thus forming a mixture comprising an oil composition having a low fatty acid content and any remaining oil fraction formed as a result of applying the first centrifugal force. The pH adjustment allows selective separation of higher quality oil while leaving the free fatty acids in an aqueous fraction by saponifying the fatty acids thus making them more water soluble. Thus, a portion of the free fatty acid is removed resulting in oil that contains low levels of free fatty acid. The age of the fermented product and the organic acid content of the fermented product can affect the optimum pH for separation, however, the oil fraction is treated with the highest pH possible to reduce the overall free fatty acid content in the separated oil without sacrificing oil quality. Any remaining fermented product fraction containing aqueous phase along with any remaining heavy components is removed. The mixture of the free oil composition and oil fraction can be removed for further processing.

In one embodiment, the pH is adjusted by introducing an inorganic base to the oil fraction. In this embodiment, the pH is increased. The inorganic base can be divalent or monovalent. Preferably, the inorganic base is a monovalent hydroxide base comprising a metal from Group I. Most preferably, the inorganic base is KOH or NaOH.

In one embodiment, the pH is adjusted to a range of about 7 to about 10. Preferably, the pH is adjusted to a range of about 7.5 to about 9.0. Most preferably, the pH is adjusted to a range of about 8.0 to about 8.5.

In one embodiment, the pH is adjusted by about 0.1% to about 99% of the original pH the oil fraction. In another embodiment, the pH is adjusted by about 20% to about 80% of the original pH the oil fraction. In yet another embodiment, the pH is adjusted by about 45% to about 65% of the original pH the oil fraction.

In one embodiment, the pH is adjusted upward by at least 0.1 pH units. In another embodiment, the pH is adjust upward by at least 0.2 pH units. In yet another embodiment, the pH is adjusted upward by at least 0.3 pH units.

In one embodiment, the pH is adjusted downward by at least 0.1 pH units. In another embodiment, the pH is adjust downward by at least 0.2 pH units. In yet another embodiment, the pH is adjusted downward by at least 0.3 pH units.

In one embodiment, the method of recovering the oil composition further comprises the step of applying a second centrifugal force to the oil fraction after adjusting the pH. In one embodiment, the centrifugal force is applied via a separator or centrifuge or a combination thereof. The second centrifugal force aids in further separating the free oil composition from the oil fraction and any remaining aqueous portion. Both the oil and oil-free fermented product are removed with the resulting oil composition being capable of direct shipment to bio-diesel producers or further refinement to edible oil standards.

In one embodiment, a second aqueous portion is formed upon application of the second centrifugal force. In one embodiment, the second aqueous portion comprises 60% to 80% moisture, based on the total weight of the second aqueous portion. In one embodiment, the second aqueous portion comprises 10% to 40% protein, based on the total weight of the second aqueous portion. In one embodiment, the second aqueous portion comprises up to 50% oil, based on the total weight of the second aqueous portion. In one embodiment, the remainder of the second aqueous portion comprises starch, neutral detergent fiber or a combination thereof. The second aqueous portion can be used to treat distillers' dried grain or other solids where an increased level of these components is desirable.

In one embodiment, the method comprises the step of recovering the oil composition from the pH adjusted oil fraction. In one embodiment, recovering the oil composition comprises separating or removing or both separating and removing the oil composition from the oil fraction after adjusting the pH. Recovering the oil composition comprises, but is not limited to, storage of the oil composition.

The oil composition recovered from the method described herein may be further processed in a variety of ways. For example, the crude oil may be filtered and bleached to provide a food grade oil for consumer use. In one embodiment, the crude oil may be degummed, further caustic refined, and subjected to a soap removal step according to commercially available processes. Following these steps the oil may then be subjected to one or more clay bleaching steps to achieve an oil of desired content and color. If one or more clay bleaching steps are used, the clay may be an acid clay or a non-acid clay. In one embodiment, the bleaching step may include, by way of example, an acid clay or a non-acid clay at 1% to 5% based on the total weight. In one embodiment, the bleaching step may include an acid clay or a non-acid clay at 2% to 4%. In another embodiment, the bleaching step may include an acid clay or a non-acid clay at 2% to 3%.

In addition to or as an alternative to clay bleaching, after the crude oil has been degummed, caustic refined and subjected to a soap removal step, a food grade oil of a desired color may be achieved using a heat bleaching step. Suitable processes for degumming, caustic refining, and soap removal are described are known by those of ordinary skill in the art. Clay bleaching and heat bleaching processes are also accessible to those of skill in the art and can be utilized to achieve a food grade oil.

The oil composition recovered from the method described herein, in one embodiment, may be used to produce bio-diesel and glycerin. There are several processes that may be used to produce bio-diesel from oils and fats, including base catalyzed transesterification, direct acid catalyzed transesterification, and conversion of the oil to its fatty acids followed by conversion of the fatty acids to bio-diesel. Bio-diesel production technologies and equipment are commercially available from, for example, Crown Iron Works Company of Minneapolis, Minn., U.S.A., and from Lurgi AG of Frankfurt, Germany. To produce bio-diesel and glycerin from the oil composition described herein, a base catalyzed transesterification process may be used.

In one embodiment, the oil composition comprises crude corn oil, and before the crude corn oil is subjected to a transesterification process, it may be pretreated. Pretreatment of the crude oil may be carried out, for example, to remove gums included in the oil or to remove or neutralize free fatty acids. As part of a degumming process, an acid, such as phosphoric acid, may be added to the crude oil and the crude oil may be heated, for example, using steam. In such a process, the acid and steam work to swell the gums so that the gums can be separated from the crude corn oil, such as by centrifugation or another suitable separation technique.

One of ordinary skill in the art appreciates that free fatty acids in the crude corn oil are generally undesirable because they tend to form soaps within the oil as they react with the base catalyst used to drive the transesterification reaction. The oil composition described herein has the advantage of containing low levels of free fatty acids thereby reducing the need for front-end or pretreatment processing in the context of bio-diesel production.

In the event pretreatment processes are utilized, such pretreatment processes may reduce the overall quality of the resulting bio-diesel and can be costly as well as inefficient. Under conventional conditions where crude corn oil is pretreated to neutralize free fatty acids, a strong base, such as NaOH (caustic soda) or KOH (potash) may be added to the crude corn oil to neutralize free fatty acids. The oil composition may be heated, for example, with steam. This process is commonly referred to as "steam stripping" and can be useful in removing free fatty acids from the oil phase.

If the oil composition is also pretreated with a degumming step, the addition of the strong base intended to neutralize the free fatty acids may occur after addition of the acid in the degumming step. In this embodiment, the base added to neutralize the free fatty acids can also work to neutralize the acid used in the degumming step. The soap stock that results from degumming and neutralization of the crude oil may be separated from the oil composition using standard equipment, such as a centrifugal separator. Alternatively, the free fatty acids can be removed and acid esterified to form bio-diesel, or combined with glycerin to form triglycerides, which are then transesterified to form bio-diesel. Pretreatment of the oil composition may also include one or more bleaching steps, such as one or more heat bleaching or clay bleaching steps, to remove residual color or other impurities from the oil composition.

Where pretreatment of the oil composition includes degumming and neutralization of free fatty acids, prior to a transesterification process, the degummed and neutralized oil is typically washed prior to transesterification. Washing may include, for example, mixing the pretreated oil with warm wash water. After washing, the oil and wash water are separated, and the pretreated oil is dried, such as by a vacuum-dryer, to a desired water content.

In one embodiment, the pretreated oil composition can be subjected to a transesterification reaction to provide bio-diesel and glycerin. The transesterification reaction is based on the chemical reaction of triglycerides contained in the oil composition with an alcohol in the presence of an alkaline catalyst. The alkaline catalyst used in the transesterification reaction may be selected from several different alkaline materials. Suitable catalysts are strong bases and include, for example, NaOH (caustic soda), KOH (potash), and $CH_3NaO$ (sodium methylate). The alcohol used in the transesterification reaction may be selected from, for example, methanol or ethanol.

As the transesterification reaction is carried out, the alcohol and catalyst may be delivered into the oil composition in parallel, as separate reaction components, or the alcohol and catalyst can be delivered to the crude oil as a mixture. When delivered as a mixture, the catalyst may be dissolved in the alcohol by any suitable means prior to charging the mixture into the oil composition. Alternatively, the catalyst may be provided as a liquid and mixed with the alcohol, limiting the need for dissolution of the catalyst in the alcohol prior to mixing the alcohol and catalyst with the oil composition. Where the catalyst is mixed with the alcohol as a liquid, the catalyst may be added to the alcohol by, for example, one or more metering pumps. In addition, because an alkaline catalyst might be sensitive to water, the catalyst may be stored in a pump tank protected with a nitrogen layer.

In carrying out the transesterification reaction, the alcohol, catalyst and oil composition may be charged into a closed reaction vessel. The reaction system can be closed to the atmosphere to prevent loss of the alcohol used in the transesterification reaction. As the reaction components are mixed, the mixture may be kept just below the boiling point of the alcohol to speed the reaction time. In addition, and excess amount of alcohol is typically used to ensure total conversion of the oil triglycerides into the desired ester product. The transesterification reaction produces a two-phase reaction product that includes an ester-rich phase (crude bio-diesel) and a glycerin-rich phase (crude glycerin). The crude glycerin is much more dense than the crude bi-diesel and the two phases can be easily separated by gravity separation or, if needed or desired, centrifugation.

In one embodiment, transesterification of the oil composition takes place in one or more mixer-settler units. In such units, the transesterification reaction occurs in a mixer or reactor included in the mixer-settler units. The crude bio-diesel and crude glycerin resulting from the transesterification reaction form two distinct phases that can be separated in the settlers. If two or more mixer-settler units are used as the reaction vessels, the feedstock and the intermediate product, respectively, may flow successively through the two or more mixer-settler units. Each mixer-settler unit can be supplied with the desired alcohol and catalyst in parallel. The reactors included in the mixer-settler units can be multi-stage in design, comprising various reaction chambers in order to achieve maximum conversion efficiency to the ester product. The settlers allow phase separation to approach the limit of solubility, which eases downstream purification of the bio-diesel and glycerin products.

At the transesterification stage, vapors vented from the reaction vessel, such as the one or more mixer-settlers, may be routed to a condenser where they are partly or completely condensed and returned to the reaction process. The same may be done with the vessel used to store or deliver the alcohol used in the transesterification reaction. Even further, where the catalyst is provided in liquid form, it too may be stored and delivered from a storage vessel, and any vapors vented from the catalyst storage vessel may also be captured, partly or completely condensed, and returned to the reaction process in liquid form.

Once the transesterification reaction is complete, at least glycerin and bio-diesel remain. The glycerin is included in the crude glycerin phase and the bio-diesel is incorporated in the crude bio-diesel phase. Each of these crude phases may include a substantial excess of the alcohol used in the reaction. Moreover, the crude reaction products may include other impurities such as excess catalyst, soaps and high boiling impurities. If desired, some of these impurities may be treated or removed from the crude reaction products before the crude bio-diesel and the crude glycerin phases are separated. For example, a suitable acid may be added to and mixed with the reaction products to neutralize excess catalyst. Additionally, excess alcohol may be removed from the crude reaction products using standard distillation equipment and techniques.

After the crude bio-diesel and crude glycerin are separated, they are typically subjected to further refining. For example, after separation, the crude bio-diesel may contain residual alcohol, glycerin, small amounts of catalyst, and soaps. This may be the case even if the crude reaction products are refined to remove or neutralize impurities prior to separation. If they have not already been refined to neutralize excess catalyst or remove excess alcohol, or if residual catalyst and excess alcohol still remain in the separated reaction products, the crude bio-diesel and crude glycerin may be treated with a suitable acid to neutralize the residual catalyst and subjected to, for example, a flash evaporation process or distillation to remove the excess alcohol.

Even where steps are taken to neutralize residual catalyst and remove excess alcohol, the refined bio-diesel may still include water soluble impurities. In order to remove such water-soluble substances, the refined bio-diesel may be washed and dried. To avoid the formation of emulsions during washing, soaps that may be present in the bio-diesel may be split, for example, by the addition of an acid to the bio-diesel to be washed. Dilute HCl, such as a 3.7% strength HCl, is suitable for such an application and can be prepared and added as necessary. The bio-diesel wash process may simply include gentle mixing of the bio-diesel with warm water, which will work to remove residual, water soluble impurities as they are taken up in the aqueous phase.

If the bio-diesel is processed through such a washing step, the refined and washed bio-diesel may contain excess water. Such excess water may be removed, for example, by subjecting the bio-diesel to a drying step. The drying step may include, for example, vacuum drying the bio-diesel to a desired water content in a dryer circuit. The dried bio-diesel, which is ready for use, distribution or sale, is collected and stored. Though the bio-diesel is serviceable at this point, if desired, it can be subjected to further distillation to remove any color bodies remaining to provide a colorless bio-diesel.

The separated, crude glycerin phase may also be further refined after separation. In particular, the crude glycerin may be neutralized with a suitable acid, the excess alcohol may be removed by distillation or flash evaporation, and the crude glycerin may be dried to remove residual water. Even if the crude reaction products of the transesterification process are neutralized and the excess alcohol present in the crude reaction products is removed prior to separation, the separated, crude glycerin may still contain residual catalyst or alcohol. Where that is the case, the separated, crude glycerin may be subjected to additional neutralization and distillation steps to neutralize any residual catalyst and remove any remaining alcohol. Once such neutralization, distillation and drying steps are complete, the crude product typically contains approximately 80-88% pure glycerin. This crude glycerin can be further refined to a purity of 99% or higher, as is known in the art, such that the glycerin product is suitable for use in cosmetic or pharmaceutical applications.

In order to minimize loss of the alcohol used in the transesterification reaction, all vessels which contain alcohol, whether in substantially pure form or as part of a crude reaction product, may be connected to a vent system to capture any alcohol vapors. Captured alcohol vapors may be fed into a condensing system that recovers the alcohol and recycles the alcohol back into the refining process.

In one embodiment, the oil composition described herein can be added to a fuel (e.g., additive). In one embodiment, the fuel can be a diesel fuel. The diesel fuel can be a hydrocarbon fuel, including but not limited to middle distillate fuels obtained from the refining of a petroleum or mineral oil source and fuels from a synthetic process such as a Fischer-Tropsch fuel from a Fischer-Tropsch process. In one embodiment, the middle distillate fuels have a distillation temperature range of 121 to 371° C., which is greater than that of gasoline or naphtha with some overlap. Middle distillate fuels include distillation fractions for diesel, jet, heating oil, gas oil, and kerosene. In another embodiment, the diesel fuel can be a bio-diesel fuel as described herein.

In one embodiment, a fuel composition is provided comprising the oil composition. In one embodiment, the fuel is a diesel fuel. In one embodiment, the fuel is a bio-diesel fuel. In one embodiment of the fuel composition, the oil composition comprises a free fatty acid content of no greater than 5% w/w based on the total weight of the composition. In another embodiment of the fuel composition, the oil composition has an iodine value of not greater than 125. In one embodiment of the fuel composition, the oil composition has a combined moisture and insoluble content of no greater than 1% w/w based on the total weight of the oil composition.

EXAMPLES

Example 1

The pH level capable of providing an oil composition containing a low level of free fatty acid was determined. First, an oil fraction in the form of an emulsion separated from fermented product was adjusted to the pH levels of 7.7, 7.9, 8.0, 8.1, 8.2, and 8.3. The samples were then centrifuged to separate the oil composition and the oil composition was analyzed for free fatty acid content. This experiment was conducted twice. The results of each experiment, Experiment 1 and Experiment 2, are shown in Table 1 and Table 2, respectively.

TABLE 1

| Experiment 1 | | | | | | |
|---|---|---|---|---|---|---|
| pH | 7.7 | 7.9 | 8.0 | 8.1 | 8.2 | 8.3 |
| Free Fatty Acid % | 3.5 | 2.2 | 2.0 | 2.2 | 2.0 | 1.8 |

TABLE 2

| Experiment 2 | | | | | | |
|---|---|---|---|---|---|---|
| pH | 7.7 | 7.9 | 8.0 | 8.1 | 8.2 | 8.3 |
| Free Fatty Acid % | 4.8 | 3.5 | 3.1 | 2.2 | 2.0 | 1.8 |

In summary, those samples tested at lower pH (i.e., below 8.0) exhibited free fatty acid contents above 3.5% w/w while those tested at a pH above 8.1 exhibited a free fatty acid content of below 2% w/w.

Example 2

Experiments were conducted to determine the amount of free oil present upon adjustment of the oil fraction to various pH levels. A series of oil fractions, in the form of emulsions samples previously separated by a first application of a centrifugal force were treated with NaOH to adjust the pH to various levels as shown in Table 3. Each sample contained the same amount of oil before adjusting the pH. After adjusting the pH to the targeted value, the volume of free oil was measured.

TABLE 3

| pH | 7.0 | 7.4 | 7.8 | 8.0 | 8.2 | 8.4 | 8.8 | 9.2 | 10.0 |
|---|---|---|---|---|---|---|---|---|---|
| Free Oil % Volume | 1.0 | 30 | 42 | 45 | 60 | 48 | 50 | 45 | 43 |

In summary, the optimum pH was obtained at about 8.2 as evidence by the highest value of free oil volume. The volume of free oil was shown to increase up to this value and then deteriorate thereafter. Thus, an optimum pH for separation exists for each oil fraction sample.

Example 3

Experiments were conducted to demonstrate that the combination of adjusting the pH and applying a centrifugal force resulted in (a) higher quality corn oil compositions and (b) higher corn oil composition yield compared to those oil compositions obtained upon application of a centrifugal force alone. The free fatty acid content was shown to be reduced by up to 3% by adjusting the pH in combination with centrifugal force as opposed to centrifugal force alone. The yield of separated oil composition was increased by 140%.

Any further modification to the present invention, which does not deviate from the scope of the appended claims as will be obvious for a person skilled in the art, is further considered to be included herein.

What is claimed is:

1. A method of recovering an oil composition comprising the steps of:
    fermenting a starch composition to form a fermented product comprising an oil fraction and a first aqueous portion;
    removing moisture from the fermented product to form a concentrated fermented product;
    separating the concentrated fermented product into an oil fraction emulsion phase and a first aqueous portion by applying a first centrifugal force, wherein the oil fraction emulsion phase comprises the oil composition and includes 20 to 70% oil and wherein the first aqueous portion includes up to 10% oil;
    treating the oil fraction emulsion phase to separate the oil composition from the emulsion forming a mixture;
    separating the mixture into the oil composition and a second aqueous portion by applying a second centrifugal force, wherein the oil composition includes 80 to 100% oil and wherein the second aqueous portion includes 50% or less oil; and
    recovering the oil composition.

2. The method of claim 1, wherein the oil fraction emulsion phase comprises from 10% to 60% moisture w/w based on the total weight of the separated oil fraction emulsion phase.

3. The method of claim 1, wherein the oil composition comprises no greater than about 2% moisture w/w and a free fatty acid content of no greater than 15% w/w based on the total weight of the oil composition.

4. The method of claim 1, wherein the treating is a pH adjustment to a range of about 3 to about 7.

5. The method of claim 4, wherein the pH is adjusted to a range of about 3.5 to about 6.

6. The method of claim 1, wherein the treating is adjusting pH by adding a base.

7. The method of claim 6, wherein the base comprise an organic base or inorganic base.

8. The method of claim 7, wherein the inorganic base comprises monovalent hydroxide base comprising a metal from Group I.

9. The method of claim 8, wherein the inorganic base comprises KOH or NaOH.

10. The method of claim 7, wherein the organic base comprise ammonia or urea.

11. The method of claim 6, wherein the pH is adjusted to a range of about 7 to about 10.

12. The method of claim 11, wherein the pH is adjusted to a range of about 7.5 to about 8.5.

13. The method of claim 12, wherein the oil composition comprises a free fatty acid content of no greater than 15% w/w based on the total weight of the oil composition.

14. The method of claim 13, wherein the free fatty acid content is no greater than 5% w/w based on the total weight of the oil composition.

15. The method of claim 14, wherein the free fatty acid content is no greater than 2% w/w based on the total weight of the oil composition.

16. The method of claim 11, wherein the pH is adjusted to a range of about 8 to about 10.

17. The method of claim 16 further comprising recovering soap from the oil composition.

18. The method of claim 1 further comprising degumming the oil composition.

19. The method of claim 18 further comprising clay bleaching, heat bleaching, transesterifying, or a combination of two or more thereof.

20. The method of claim 1 further comprising cooking the starch composition or adding an enzyme composition before forming the fermented product.

21. The method of claim 1, wherein the starch composition is not cooked before providing forming the fermented product.

22. The method of claim 1, wherein the fermented product has a moisture content of 60% to 95%.

23. The method of claim 1, wherein the concentrated fermented product is a syrup.

* * * * *